United States Patent [19]

Mifune et al.

[11] 4,418,140
[45] Nov. 29, 1983

[54] PROCESS FOR THE DEVELOPMENT OF COLOR PHOTOGRAPHIC LIGHT-SENSITIVE MATERIAL

[75] Inventors: Hiroyuki Mifune; Shoji Ishiguro; Tadao Shishido, all of Minami-ashigara; Tatsuo Nishimura, Ashiya, all of Japan

[73] Assignee: Fuji Photo Film Co., Ltd., Kanagawa, Japan

[21] Appl. No.: 366,515

[22] Filed: Apr. 8, 1982

[30] Foreign Application Priority Data

Apr. 8, 1981 [JP] Japan .................................. 56-52771

[51] Int. Cl.³ ................................................ G03C 7/00
[52] U.S. Cl. .................................... 430/351; 430/372; 430/377; 430/445; 430/489; 430/490; 430/551; 430/622
[58] Field of Search ............... 430/372, 445, 489, 490, 430/551, 622, 377, 351

[56] References Cited

U.S. PATENT DOCUMENTS

| | | | |
|---|---|---|---|
| 3,266,897 | 8/1966 | Kennard et al. | 430/445 |
| 4,021,248 | 5/1977 | Shiba et al. | 430/551 |
| 4,250,252 | 2/1981 | Odenwalder et al. | 430/445 |
| 4,328,302 | 5/1982 | Nishimura et al. | 430/445 |

*Primary Examiner*—J. Travis Brown

*Attorney, Agent, or Firm*—Sughrue, Mion, Zinn, Macpeak and Seas

[57] ABSTRACT

A process for the development of color photographic light-sensitive material is described. The process comprises color developing an exposed light-sensitive material in the presence of a compound of the general formula:

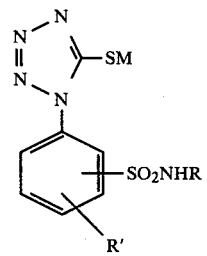

wherein M is a hydrogen atom, an alkali metal atom, $NH_4$ or a protective group for the mercapto group which undergoes cleavage by the action of an alkali; R is a hydrogen atom or an alkyl group containing 1 to 3 carbon atoms; and R' is a hydrogen atom or an alkyl group containing 1 to 3 carbon atoms. This process prevents the formation of color development fog without seriously reducing sensitivity.

11 Claims, 1 Drawing Figure

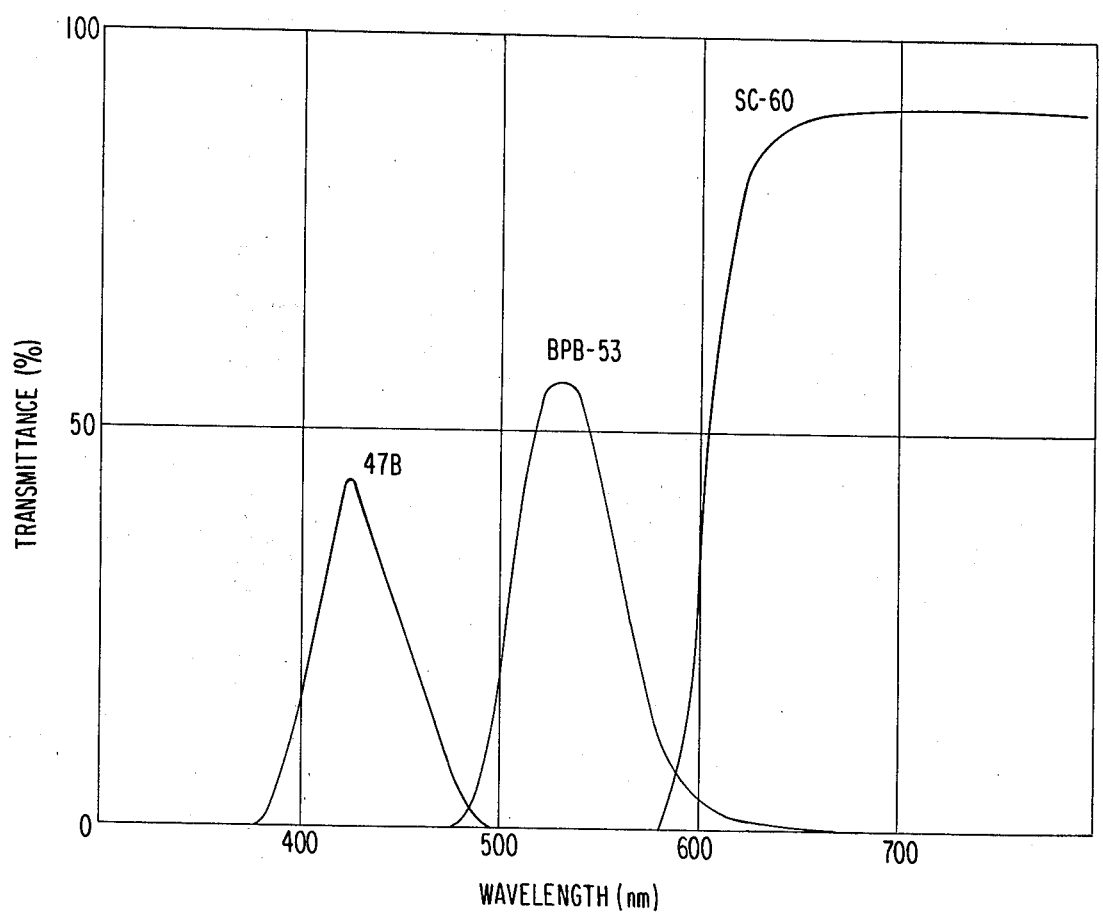

PROCESS FOR THE DEVELOPMENT OF COLOR PHOTOGRAPHIC LIGHT-SENSITIVE MATERIAL

FIELD OF THE INVENTION

The present invention relates to a process for developing color photographic light-sensitive materials, and more particularly, to a process of development which effectively prevents the formation of development fog while minimizing the inhibition of color development and reduction of sensitivity.

BACKGROUND OF THE INVENTION

The increase in dye density of unexposed areas in color photographic light-sensitive material on application of color development (in the case of reversal light-sensitive material, the dye density of unexposed areas decreases) is called "formation of color development fog", This phenomenon usually occurs more readily with an increase in the sensitivity of color photographic light-sensitive materials. The phenomenon is also more likely to occur as the period for which the color photographic light-sensitive material is stored is lengthened. Furthermore, the phenomenon occurs more readily if the light-sensitive material is stored in a higher temperature or humidity. Moreover, as the color developing temperature is increased, the phenomenon occurs more easily. It is preferable to control the formation of color development fog to as low a level as possible since wt causes deterioration of photographic properties, e.g., a reduction in image contrast.

In order to prevent the formation of color development fog, there has heretofore been used a method in which substances called "antifoggants" are incorporated into light-sensitive materials or developers. A number of compounds are known as antifoggants. Of these compounds, 1-phenyl-5-mercaptotetrazole is most widely used. This compound, however, is not suitable particularly for a forced development, in which a time for development (including first development in a reversal development) is lengthened than a normal developing time (which is usually specified by each maker of a photographic light-sensitive material although the normal developing time varies due to a development processing, see, *Photo. Lab. Index,* Morgan & Morgan Inc., etc.) so as to obtain higher sensitivity than the sensitivity obtained by the normal developing time, since it often causes a considerable reduction in sensitivity due to its too high ability to prevent color development.

Other known antifoggants include 1-phenyl-5-mercaptotetrazole derivatives, as described in U.S. Pat. No. 3,266,897, in which the phenyl group is substituted by two carboxyl groups. However, these compounds are not good for preventing the formation of color development fog for light-sensitive materials which have been stored under high temperature and humidity conditions.

SUMMARY OF THE INVENTION

An object of the invention is to provide a process for the development of color photographic light-sensitive materials, which overcomes the above-described defects by effectively preventing the formation of color development fog while minimizing any reduction in sensitivity.

Another object of the invention is to provide a process for the development of color photographic light-sensitive materials. The process prevents the formation of color development fog accompanied by only a small reduction in sensitivity even for color photographic light-sensitive materials which have been stored under high temperature and humidity conditions.

A further object of the invention is to provide a process for the development of color photographic light-sensitive materials, which is an efficient forced development involving lengthening the developing time for color development, while preventing the formation of color development fog.

The present inventors have found that these and other objects can be attained by color developing exposed color photographic light-sensitive materials in the presence of the compounds represented by the following general formula:

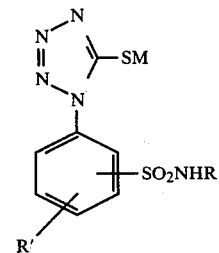

The symbols used in the general formula are defined hereinafter.

The present invention, therefore, relates to a process for developing a color photographic light-sensitive material which comprises exposing the material and color developing the material in the presence of a compound represented by the general formula as defined above.

BRIEF DESCRIPTION OF THE DRAWINGS

The FIGURE is a graph showing the spectral transmittance for each separation filter used in Example 4.

DETAILED DESCRIPTION OF THE INVENTION

In the general formula as described above, M is a hydrogen atom, an alkali metal atom, $NH_4$ or a protective group for the mercapto group, which undergoes cleavage by the action of alkali. Alkali metal atoms include a sodium atom, a potassium atom, and a lithium atom. Protective groups for the mercapto group which undergo cleavage by the action of alkali include a group $-CH_2-CH_2-CN$ and a group

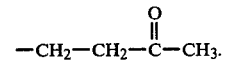

Particularly preferred examples of M are a hydrogen atom and a sodium atom.

R is a hydrogen atom or an alkyl group containing 1 to 3 carbon atoms, e.g., a methyl group, an ethyl group, a propyl group, and an isopropyl group. A hydrogen atom is particularly preferred.

R' is a hydrogen atom or an alkyl group containing 1 to 3 carbon atoms, e.g., a methyl group, an ethyl group, a propyl group, and an isopropyl group. A hydrogen atom is particularly preferred.

Although the group $-SO_2NHR$ may be positioned at any location of the benzene nucleus, it is particularly preferred to be linked at the para-position relative to the carbon atom that is bound to the nitrogen atom of the tetrazole group.

Suitable examples of the compounds represented by the general formula as defined above are set forth below:

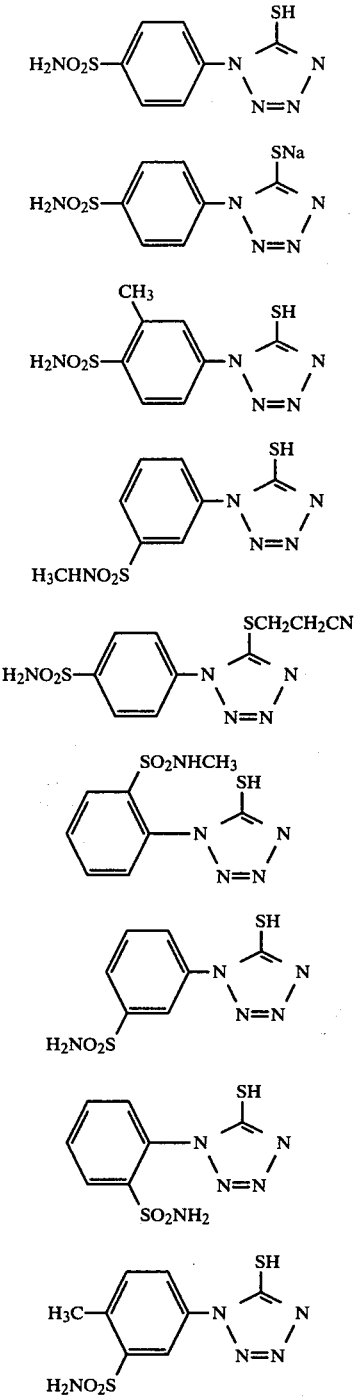

Of the above example compounds, all compounds are preferred for the present invention, and particularly preferred compounds are Compounds 1, 2, 3 and 5.

These compounds can be prepared easily. For example, a compound of the formula:

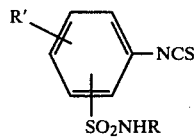

is prepared from a compound of the formula:

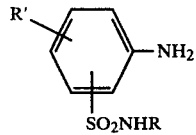

by known techniques, e.g., by reacting with phosgene, and then reacting with sodium azide.

For further details of the process and so forth, it is possible to refer to, for example, British Pat. No. 1,275,701, U.S. Pat. No. 3,266,897, and G. Dubenko & V. D. Panchenco, Khim. Geterotsikl. Soedin., Sb-1; Azots order zhaschie Geterotsikly, pp. 199 to 201 (1967), and C. F. H. Allen, Can. J. Chem., 44, 2315 (1966) each being incorporated herein by reference.

An example of the preparation of the present compounds is described below:

PREPARATION EXAMPLE

Synthesis of Compound 1

To 100 ml of water was added 25 g of thiophosgene, and 30 g of p-aminobenzenesulfonamide was added thereto at room temperature while fully stirring. The mixture was stirred for 2 hours. At the end of the time, precipitated crystals were collected, and 33 g of crude crystals of isothiocyanate were obtained. m.p.: 208° to 209° C. (decomposition).

A mixture of 33 g of the isocyanate, 400 ml of water and 15 g of sodium azide was heated to reflux for 3 hours. The resulting mixture was filtered while it was hot, and the filtrate was cooled and made alkaline by addition of diluted hydrochloric acid. Precipitates were collected by filtration and recrystallized from methanol-water. Thus, 19.5 g of Compound 1 was obtained. m.p.: 166° to 167° C. (decomposition).

The compounds other than Compound 1 can be synthesized very easily according to the above described preparation example.

In accordance with the process of development of the invention, color development of exposed color photographic light-sensitive materials using known color developers is conducted in the presence of the compounds of the above-described general formula.

The color development in the presence of the compounds of the invention can be performed in various manners. That is, the compound of the invention can be incorporated into the color photographic light-sensitive materials, particularly into the emulsion layer or other hydrophilic colloid layer at the step of production, or it can be incorporated into the color developer or the prebath (including a first developer in a color reversal process) before the color development. Particularly preferred embodiment of the present invention is that the compound of the present invention is incorporated into the color photographic light-sensitive material.

Since the compounds of the invention are water-soluble, the process of incorporation can be performed conveniently, and problems do not arise in adding them in such amounts as to produce the effect of preventing the formation of color development fog. Although the compound of the invention can be added in such amounts as to produce the effect of preventing color development fog, when it is incorporated into the light-sensitive material, the amount is usually from $10^{-7}$ to $10^{-2}$ mol/Ag mol and preferably from $10^{-6}$ to $10^{-2}$ mol/Ag mol, and when it is incorporated into the color developer, the amount is usually from $10^{-6}$ to $10^{-1}$ mol/l and preferably from $10^{-5}$ to $3\times10^{-2}$ mol/l.

The process of development of the invention can be conducted using known color developers and developing techniques (as described, for example, in T. H. James, *The Theory of the Photographic Process*, 4th Ed., pages 335–372 et seq., (1977), Macmillan Publishing Co., Inc.) except that it is performed in the presence of the compounds of the invention.

The processing temperature is ordinarily chosen within the range of from 18° to 50° C., although it may be lower than 18° C. or higher than 50° C. The processing time is ordinarily chosen within the range of from 10 seconds to 12 minutes, although it varies depending on the developing temperature.

Color developing processings which can be used include a negative-positive process (as described in, for example, *Journal of the Society of Motion Picture and Television Engineers*, Vol. 61, pp 667–701 (1953) incorporated herein by reference), and a color reversal process in which a light-sensitive material is developed with a developer containing a black-and-white developing agent to form a negative silver image, and is subjected to at least one uniform exposure or other suitable fogging treatment, and subsequently, color development is conducted to obtain a positive dye image.

The color developer is generally composed of an alkaline aqueous solution containing a color developing agent. Color developing agents which can be used include known primary aromatic amine developers, e.g., phenylenediamines such as 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, and 4-amino-3-methyl-N-ethyl-N-β-methoxyethylaniline.

In addition, the compounds described in L.F.A. Mason, *Photographic Processing Chemistry*, Focal Press, pp. 226–229 (1966), U.S. Pat. Nos. 2,193,015, 2,592,364, Japanese Patent Application (OPI) No. 64933/73 (the term "OPI⇌ as used herein refers to a "published unexamined Japanese patent application"), etc.

The color developer can further contain pH buffers, e.g., sulfites, carbonates, borates and phosphates of alkali metals, development inhibitors or antifoggants, e.g., bromides, iodides and organic antifoggants, and so forth. In addition, if necessary, it may contain hard water-softening agents, preservatives, e.g., hydroxyamines, organic solvents, e.g., benzyl alcohol and diethylene glycol, development accelerators, e.g., polyethylene glycol, quaternary ammonium salts, and amines, dye-forming couplers, competing couplers, fogging agents, e.g., sodium borohydride, auxiliary agents of developer, e.g., 1-phenyl-3-pyrazolidone, tackifiers, the polycarboxylic acid-based chelating agents described in U.S. Pat. No. 4,083,723, the antioxidants described in West German Patent Application (OLS) No. 2,622,950, and so forth.

After the color development, the photographic emulsion layer is usually bleached. The bleaching processing may be carried out simultaneously with the fixing processing or be carried out separately.

Bleaching agents which can be used include compounds of multivalent metals, e.g., iron (III), cobalt (III), chromium (VI), and copper (II), peracids, quinones, and nitroso compounds. Examples are ferricyanides, dichromic acid salts, organic complex salts of iron (III) and cobalt (III), aminopolycarboxylic acid salts, e.g., ethylenediaminetetraacetic acid, nitrilotriacetic acid, and 1,3-diamino-2-propanol tetraacetic acid, complex salts of organic acids, e.g., citric acid, tartaric acid, and phosphoric acid, persulfuric acid salts, permanganic acid salts, and nitrosophenol. Of these compounds, potassium ferricyanide, iron (III) sodium ethylenediaminetetraacetate, and iron (III) ammonium ethylenediaminetetraacetate are particularly useful. Ethylenediaminetetraacetic acid iron (III) complex salts are useful both in an independent bleaching liquid and in a combined bleaching and fixing liquid.

The bleaching or bleach-fixing liquid can be added various additives as well as the bleach accelerators described in, for example, U.S. Pat. Nos. 3,042,520, 3,241,966, and Japanese Patent Publication Nos. 8506/70, and 8836/70, and the thiol compounds described in Japanese Patent Application (OPI) No. 65732/78.

The process of development of the invention can be applied to color photographic light-sensitive materials which are prepared using known various silver halide emulsions.

Silver halide emulsions to which the process of the invention can be applied include silver chloride, silver bromide, silver chlorobromide, silver iodide, silver iodobromide, and silver chloroiodobromide. Preferred silver halide emulsions are silver halide emulsions other than silver chloride. The emulsion may be chemically sensitized by instable sulfur compounds or gold compounds or combinations thereof. Furthermore, the emulsion may be color sensitized by cyanine dyes, merocyanine dyes, and so forth. Moreover, the emulsion may be stabilized by heterocyclic compounds, e.g., 4-hydroxy-6-methyl-1,3,3a,7-tetraazaindene.

The photographic emulsion or color developer as used herein contains dye-forming couplers, i.e., compounds capable of forming color by oxidative coupling with aromatic primary amine developers (e.g., phenylenediamine derivatives and aminophenol derivatives) in the color developing processing. Couplers which can be used as magenta couplers include a 5-pyrazolone coupler, a pyrazolobenzimidazole coupler, a cyanoacetylcumarone coupler, and an open chain acylacetonitrile coupler. Examples of yellow couplers include acylacetamide couplers, e.g., benzoacetanilides and pivaloylacetanilides. Examples of cyan couplers include a naphthol coupler and a phenol coupler. It is preferred for these couplers to contain a hydrophobic group called a ballast group and to be non-diffusing. The coupler may be 4-equivalent or 2-equivalent for a silver ion. Furthermore, it may be a colored coupler having the effect of color correction, or a coupler (so-called DIR coupler) releasing a development inhibitor with development. Moreover, other than the DIR coupler, it may contain a colorless compound-forming DIR coupling compound that yields a colorless coupling reaction product and releases a development inhibitor.

Suitable examples of magenta couplers are described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, 3,891,445, West German Pat. No. 1,810,464, West German Patent Application (OLS) Nos. 2,408,665, 2,417,945, 2,418,959, 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76, 55122/78, etc.

Suitable examples of yellow couplers are described in U.S. Pat. Nos. 2,875,057, 3,265,506, 3,408,194, 3,551,155, 3,582,322, 3,725,072, 3,891,445, West German Pat. No. 1,547,868, West German Patent Application Laid-Open Nos. 2,219,917, 2,261,361, 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77, 1152219/77, etc.

Suitable examples of cyan couplers are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, 4,004,929, West German Patent Application (OLS) Nos. 2,414,830, 2,454,329, Japanese Patent Application (OPI) Nos. 59838/73, 26034/76, 5055/73, 146828/76, 69624/77, 90932/77, etc.

Colored couplers which can be used include those described in U.S. Pat. Nos. 3,476,560, 2,521,908, 3,034,892, Japanese Patent Publication Nos. 2016/69, 22335/63, 11304/67, 32461/69, Japanese Patent Application (OPI) Nos. 26034/76, 42121/77, and West German Patent Application (OLS) No. 2,418,959.

DIR couplers which can be used include those described in U.S. Pat. Nos. 3,227,554, 3,617,291, 3,701,783, 3,790,384, 3,632,345, West German Patent Application (OLS) Nos. 2,414,006, 2,454,301, 2,454,329, British Pat. No. 953,454, Japanese Patent Application (OPI) Nos. 69624/77, 122335/74, and Japanese Patent Publication No. 16141/76.

The light-sensitive material may contain those compounds releasing a development inhibitor with development. For example, the compounds described in U.S. Pat. Nos. 3,297,445, 3,379,529, West German Patent Application (OLS) No. 2,417,914, Japanese Patent Application (OPI) Nos. 15271/77 and 9116/78.

The incorporation of the coupler into the silver halide emulsion layer can be conducted by known techniques, e.g., the method described in U.S. Pat. No. 2,322,027. For example, the coupler is dissolved in an organic solvent and, thereafter, dispersed in hydrophilic colloid. Organic solvents which can be used include alkyl phthalates, e.g., dibutyl phthalate and dioctyl phthalate, phosphates, e.g., diphenyl phosphate, triphenyl phosphate, tricresyl phosphate, and dioctyl butylphosphate, citrates, e.g., tributyl acetylcitrate, benzoates, e.g., octyl benzoate, alkylamides, e.g., diethyllaurylamide, aliphatic acid esters, e.g., dibutoxyethyl succinate and dioctyl azelate, trimesic acid esters, e.g., tributyl trimesate, and organic solvents having boiling points of from about 30° to 150° C., e.g., lower alkyl acetates such as ethyl acetate and butyl acetate, ethyl propionate, sec-butyl alcohol, methyl isobutyl ketone, β-ethoxyethyl acetate, and methyl cellosolve acetate. These high boiling organic solvents and low boiling organic solvents can be used in combination with each other.

The emulsion or coating solutions for the preparation of other layers may contain organic or inorganic hardeners, e.g., chromium salts, such as chromium alum and chromium acetate, aldehydes, such as formaldehyde, glyoxal, and glutaraldehyde, N-methylol compounds, such as dimethylol urea and methylol dimethylhydantoin, dioxane derivatives, such as 2,3-dihydroxydioxane, active vinyl compounds, such as 1,3,5-triacryloyl-hexahydro-s-triazine and 1,3-vinylsulfonyl-2-propanol, active halogeneous compounds, such as 2,4-dichloro-6-hydroxy-s-triazine, and mucohalogenic acids, such as mucochloric acid and mucophenoxychloric acid. Of the above hardeners, a vinyl sulfone-based compound (for example, 1-vinylsulfonyl-2-propanol) is preferred from a viewpoint of hardening, but the vinyl sulfone-based compound has a defect of forming color development fog.

The process of development of the invention is very effective in preventing the formation of color development fog observed when a color photographic light-sensitive material containing a vinyl sulfone-based compound as a hardener, particularly a reversal color photographic light-sensitive material is stored at high temperatures or at high temperatures and humidities (in the case of the reversal color photographic light-sensitive material, this is observed as a reduction in the maximum image density).

Vinyl sulfone-based hardeners which can be used are described in, for example, Japanese Patent Application (OPI) Nos. 41221/78, 57257/78, 126124/76, Japanese Patent Publication No. 13563/74, Japanese Patent Application (OPI) Nos.44164/76, 21059/77, U.S. Pat. Nos. 3,490,911, 3,539,644, Japanese Patent Publication No. 35807/75, Japanese Patent Application (OPI) Nos. 30022/79, 66960/78, Japanese Patent Publication Nos. 46495/77 and 8736/72.

Suitable examples of such vinyl sulfone-based hardeners are listed below:

Compound V-1
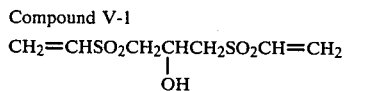

Compound V-2
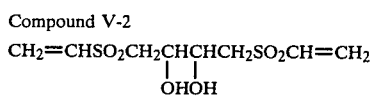

Compound V-3
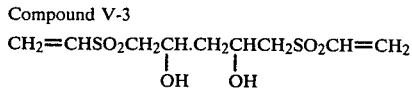

Compound V-4
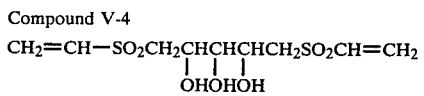

Compound V-5
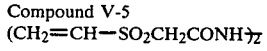

Compound V-6
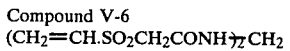

Compound V-7
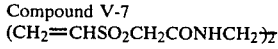

Compound V-8
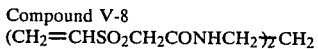

Compound V-9

CH$_2$=CH.SO$_2$CH$_2$CON(piperazine)NCOCH$_2$SO$_2$CH=CH$_2$

Compound V-10

CH$_2$=CHSO$_2$CH$_2$CON(piperazine with N-COCH$_2$SO$_2$CH=CH$_2$ and N-COCH$_2$SO$_2$CH=CH$_2$)

Compound V-11

CH$_2$=CH.SO$_2$CH$_2$CH$_2$COON(succinimide)

Compound V-12

CH$_2$=CH.SO$_2$CH$_2$CH$_2$COOCH$_2$-$\overset{\oplus}{N}$(piperidine)NCl$^{\ominus}$ Compound V-13
CH$_2$=CHSO$_2$CH$_2$SO$_2$CH=CH$_2$ Compound V-14
CH$_2$=CH.SO$_2$CH$_2$CH$_2$SO$_2$CH=CH$_2$ Compound V-15
CH$_2$=CH.SO$_2$CH$_2$CH$_2$CH$_2$SO$_2$CH=CH$_2$ Compound V-16
CH$_2$=CH.SO$_2$N(piperazine)NSO$_2$CH=CH$_2$ Compound V-17
C$_2$H$_5$—C(CH$_2$SO$_2$CH=CH$_2$)$_3$ Compound V-18
CH$_2$=CHSO$_2$CH$_2$CH.CH$_2$SO$_2$CH=CH$_2$
            |
            SO$_2$CH=CH$_2$ Compound V-19 benzene with SO$_2$CH=CH$_2$, CH$_2$=CHSO$_2$, SO$_2$CH=CH$_2$ substituents (1,3,5)

Compound V-20 benzene with CH$_2$SO$_2$CH=CH$_2$, CH$_2$=CHSO$_2$CH$_2$, CH$_2$SO$_2$CH=CH$_2$ substituents (1,3,5)

Compound V-21
(CH$_2$=CHSO$_2$CH$_2$)$_4$C

Compound V-22
(CH$_2$=CHSO$_2$CH$_2$)$_3$CCH$_2$SO$_2$CH=CHNHCH$_2$CH$_2$SO$_3$Na Compound V-23
CH$_2$=CHSO$_2$C$_2$H$_4$CONH      NHCOC$_2$H$_4$SO$_2$CH=CH$_2$
                       CHCH$_2$CH
CH$_2$=CHSO$_2$C$_2$H$_4$CONH      NHCOC$_2$H$_4$SO$_2$CH=CH$_2$ Compound V-24

CH$_2$=CHSO$_2$N(piperazine ring with H$_2$ groups)NSO$_2$CH=CH$_2$, with N-SO$_2$CH=CH$_2$ Compound V-25

CH$_2$=CHSO$_2$CH$_2$CH$_2$N(piperazine)N—CH$_2$CH$_2$SO$_2$CH=CH$_2$

Compound V-26

CH$_2$=CHSO$_2$CH$_2$CH$_2$—$\overset{\oplus}{N}$(piperazine with H$_3$C, CH$_3$)$\overset{\oplus}{N}$CH$_2$CH$_2$SO$_2$CH=CH$_2$
2ClO$_4$ Compound V-27

CH$_2$=CHSO$_2$CH$_2$CH$_2$$\overset{\oplus}{N}$(CH$_3$)$_2$—CH$_2$CH$_2$CH$_2$CH$_2$$\overset{\oplus}{N}$(CH$_3$)$_2$—CH$_2$CH$_2$SO$_2$CH=CH$_2$
2(CH$_3$—C$_6$H$_4$—SO$_3^{\ominus}$)

Compound V-28
CH$_2$=CHSO$_2$CH$_2$CH$_2$SO$_2$CH$_2$CH$_2$SO$_2$CH=CH$_2$

Compound V-29
CH$_2$=CHSO$_2$CH$_2$CH$_2$OCH$_2$CH$_2$NHCONHCH$_2$CH$_2$OCH$_2$CH$_2$SO$_2$CH=CH$_2$ Compound V-30
CH$_2$=CHSO$_2$CH$_2$CH$_2$OCH$_2$CH$_2$OCH$_2$CH$_2$SO$_2$CH=CH$_2$ Compound V-31
CH$_2$=CHSO$_2$CH$_2$OCH$_2$SO$_2$CH=CH$_2$ Compound V-32
CH₂=CHSO₂CH₂CH₂OCH₂CH₂SO₂CH=CH₂

Compound V-33
CH₂=CHSO₂CH₂CH₂CH₂CH₂OCH₂CH₂CH₂CH₂SO₂CH=CH₂

Compound V-34
(CH₂=CH.SO₂CH₂CH₂CONH)₂CH₂

Compound V-35
(CH₂=CH—SO₂CH₂CH₂CONH.CH₂)₂

Compound V-36
(CH₂=CH—SO₂CH₂CH₂CONHCH₂)₂CH₂

Compound V-37

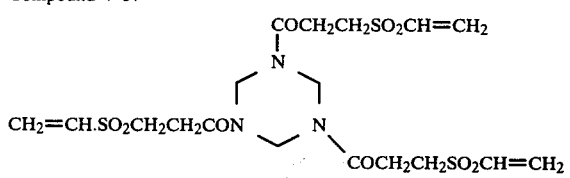

Compound V-38
CH₂=CHSO₂CH=CH₂

Compound V-39

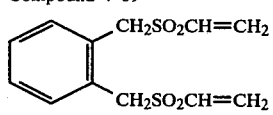

Compound V-40

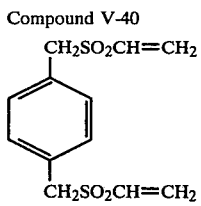

Of the above hardeners, all hardeners are preferred for the present invention, and particularly preferred hardeners are Compounds V-1, V-6, V-7, V-9, V-10, V-13, V-14, V-15, V-21, V-22, V-25, V-31, V-32, V-34, V-35, V-36 and V-37.

The amount of the hardener used can be determined at will depending on the purpose. It is usually from 0.01 to 20% by weight and preferably from 0.1 to 10% by weight, based on the weight of dry gelatin.

In addition, various known additives, e.g., surface active agents as coating aids, latexes for dimensional stability, whiteners, color image-forming couplers, DIR couplers, color-mixing preventing agents, ultraviolet absorbers, antifading agents, and mordants can be added to the photographic emulsion. Details are known as described in, for example, Research Disclosure, No. 17643, December 1978, pp. 22–31.

Since the process of the invention uses a novel antifoggant, it greatly aids in preventing the formation of color development fog while minimizing the reduction in sensitivity. Furthermore, in the forced development in which the color development is performed for a prolonged period of time, it allows for effective sensitization while preventing the formation of color development fog. Furthermore, the formation of color development fog which occurs when a color photographic light-sensitive material containing a vinyl sulfone-based hardener, particularly a reversal color photographic light-sensitive material is stored for a long period of time can be prevented effectively.

The following Examples are given to illustrate the invention in greater detail.

EXAMPLE 1

To a silver iodobromide gelatin emulsion (mean size of silver halide grains; 0.95 micron) containing 8.5 mol% of silver iodide were added potassium chlorooleate, Rhodan ammonium, and sodium thiosulfate. The mixture was ripened by heating at 60° C. for 60 minutes. To the thus-prepared emulsion a compound of the invention or a comparative compound was added as indicated in Table 1, and the additives as set forth hereinafter. The resulting mixture was coated and dried to prepare Samples 1, 2, 3, 4, 5 or 6.

Additives

Coupler: 1-(2,4,6-Trichlorophenyl)-3-[3-(2,4-di-tert-amylphenoxy)acetamido]benzamido-5-pyrazolone Spectral sensitizer: Bis{2-[1-ethyl-3-(3-sulfopropyl)-5,6-dichlorobenzimidazole]}trimethinecyanine sodium salt Stabilizer: 4-Hydroxy-6-methyl-1,3,3a,7-tetraazaindene Hardener: 2,4-Dichloro-6-hydroxy-1,3,5-triazine sodium salt Coating aids: Sodium p-dodecylbenzenesulfonate and sodium p-nonylphenoxypoly(ethyleneoxy)propanesulfonate Each sample was exposed to light through a yellow filter for 1/20 second, color developed by the process as described hereinafter, and thereafter, the photographic properties were measured with the results shown in Table 1.

In Table 1, the sensitivity is a reciprocal number of the logarithm of an exposure amount necessary for obtaining an optical density of a color development fog value of +0.2, and is indicated as a relative value with that of Sample 1 as 100.

Process

| | | |
|---|---|---|
| 1. | Color development | 3.25 min (38° C.) |
| 2. | Bleaching | 6.5 min |
| 3. | Water-washing | 3.25 min |
| 4. | Fixing | 6.5 min |
| 5. | Water-washing | 3.25 min |
| 6. | Stabilization | 3.25 min |

The composition of the processing solution used at each step is shown below:

Color Developer

| | |
|---|---|
| Sodium nitrilotriacetate | 1.0 g |
| Sodium sulfite | 4.0 g |
| Sodium carbonate | 30.0 g |
| Potassium bromide | 1.4 g |
| Hydroxylamine sulfuric acid salt | 2.4 g |
| 4-(N—Ethyl-N—β-hydroxyethylamino)-2-methylaniline sulfuric acid salt | 4.5 g |
| Water to make | 1 liter |

Bleaching Solution

| | |
|---|---|
| Ammonium bromide | 160.0 g |
| Ammonium water (28%) | 25.0 ml |
| Ethylenediaminetetraacetic acid Sodium iron salt | 130 g |
| Glacial acetic acid | 14 ml |
| Water to make | 1 liter |

Fixing Solution

| | |
|---|---|
| Sodium tetrapolyphosphate | 2.0 g |
| Sodium sulfite | 4.0 g |
| Ammonium thiosulfate (70%) | 175.0 ml |
| Sodium hydrogensulfite | 4.6 g |
| Water to make | 1 liter |

Stabilizing Solution

| | |
|---|---|
| Formalin | 8.0 ml |
| Water to make | 1 liter |

TABLE 1

| Sample | Compound | Amount (mol/mol AgX) | Color Development Fog Density | Relative Sensitivity |
|---|---|---|---|---|
| 1 (control) | Not added | — | 0.25 | 100 |
| 2 (the invention) | Compound 1 | $1.3 \times 10^{-4}$ | 0.08 | 88 |
| 3 (the invention) | Compound 1 | $3.0 \times 10^{-4}$ | 0.04 | 82 |
| 4 (the invention) | Compound 3 | $2.1 \times 10^{-4}$ | 0.05 | 84 |
| 5 (the invention) | Compound 5 | $1.2 \times 10^{-3}$ | 0.04 | 87 |
| 6 (comparison) | Comparative Compound (a) | $2.1 \times 10^{-4}$ | 0.04 | 70 |

Comparative Compound (a):

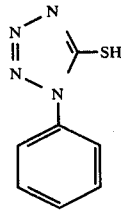

It can be seen from Table 1 that the compounds of the invention offer the advantage over Comparative Compound (a), which is an antifoggant well known in this field, in that there is less reduction in sensitivity while the formation of color development fog is prevented to the same level as with the comparative examples.

EXAMPLE 2

In order to examine changes in the formation of color development fog and sensitivity for each sample prepared in Example 1 when a sensitizing processing is performed by prolonging the color developing time, the procedure of Example 1 was repeated with the exception that the color developing time was prolonged to 4 minutes and 53 seconds (38° C.). The results are shown in Table 2. For the convenience of comparison, the results of Example 1 are again listed.

TABLE 2

| | Color Development (3.25 min) | | Color Development (4 min and 53 sec) | |
|---|---|---|---|---|
| Sample | Color Development Fog | Relative Sensitivity | Color Development Fog | Relative Sensitivity |
| 1 (control) | 0.25 | 100 | 0.49 | 195 |
| 2 (the invention) | 0.08 | 88 | 0.20 | 163 |
| 3 (the invention) | 0.04 | 82 | 0.13 | 150 |
| 4 (the invention) | 0.05 | 84 | 0.16 | 155 |
| 5 (the invention) | 0.04 | 87 | 0.09 | 150 |
| 6 (comparison) | 0.04 | 70 | 0.12 | 115 |

It can be seen from Table 2 that the compounds of the invention exhibit less inhibition of the color development while preventing the formation of color development fog. Furthermore, within the sensitizing processing, they permit an increase in the sensitivity without seriously causing the formation of color development fog. On the other hand, the color light-sensitive material using Comparative Compound (a), which is a known antifoggant, is not suitable for use in the sensitizing processing in which the color development is performed for a prolonged period of time since it seriously inhibits the color development.

EXAMPLE 3

To a silver chlorobromide emulsion (Br content: 90 mol%; Cl content: 10 mol%; mean grain size: about 0.7 micron) were added a compound of the invention or a comparative compound as indicated in Table 3, and the additives as described hereinafter. The resulting mixture was coated on a photographic paper which had been covered with a polyethylene film to prepare Sample 10, 11, 12 or 13.

Each sample was exposed to light through an optical wedge and color developed by the process as described hereinafter, and thereafter, the photographic properties were measured with the results shown in Table 3.

Additives

Yellow coupler: α-(4-Palmitamidophenoxy)-α-pivaloyl-4-sulfoamylacetanilide

Stain inhibitor: 2-n-Octadecyl-5-(2-sulfo-tert-butyl)-halidoquinone potassium salt Stabilizer: 4-Hydroxy-6-methyl-1,3,3a,7-tetraazaindene Hardener: 2,4-Dichloro-6-hydroxy-1,3,5-triazine sodium salt Coating aids: Sodium p-dodecylbenzenesulfonate and sodium p-nonylphenoxypoly(ethyleneoxy)propanesulfonate

Process

| | Temperature (°C.) | Processing (A) Time (min) | Processing (B) Time (min) |
|---|---|---|---|
| 1. Color Development | 30 | 6 | 9 |
| 2. Stopping | 30 | 2 | 2 |
| 3. Water-Washing | 30 | 2 | 2 |
| 4. Bleach-Fixing | 30 | 1.5 | 1.5 |
| 5. Water-Washing | 30 | 2 | 2 |
| 6. Stabilizing Bath | 30 | 2 | 2 |
| 7. Drying | | | |

The composition of the processing solution used at each step is shown below:

Color Developer

| | | |
|---|---|---|
| Benzyl alcohol | 12 | ml |
| Diethylene glycol | 3.5 | ml |
| Sodium hydroxide | 2.0 | g |
| Sodium sulfite | 2.0 | g |
| Potassium bromide | 0.4 | g |
| Sodium chloride | 1.0 | g |
| Borax | 4.0 | g |
| Hydroxylamine sulfuric acid salt | 2.0 | g |
| Disodium ethylenediaminetetraacetate dihydrate | 2.0 | g |
| 4-Amino-3-methyl-N—ethyl-N—(β-methanesulfonamidoethyl)aniline sesquisulfate monohydrate | 5.0 | g |
| Water to make | 1 | liter |

Stopping Solution

| | | |
|---|---|---|
| Sodium thiosulfate | 10 | g |
| Ammonium thiosulfate (70%) | 30 | ml |
| Sodium acetate | 5 | g |
| Acetic acid | 30 | ml |
| Potash alum | 15 | g |
| Water to make | 1 | liter |

Bleach-Fixing Solution

| | | |
|---|---|---|
| Ferric sulfate | 20 | g |
| Disodium ethylenediaminetetraacetate dihydrate | 36 | g |
| Sodium carbonate monohydrate | 17 | g |
| Sodium sulfite | 5 | g |
| 70% Aqueous solution of ammonium thiosulfate | 100 | ml |
| Boric acid (adjusted to pH 6.8) | 5 | g |
| Water to make | 1 | liter |

Stabilizing Solution

| | | |
|---|---|---|
| Boric acid | 5 | g |
| Sodium citrate | 5 | g |
| Sodium metaborate tetrahydrate | 3 | g |
| Potash alum | 15 | g |
| Water to make | 1 | liter |

TABLE 3

| Sample | Compound | Amount (mol/mol AgX) | Processing (A) Color Development Fog | Processing (A) Relative Sensitivity | Processing (B) Color Development Fog | Processing (B) Relative Sensitivity |
|---|---|---|---|---|---|---|
| 10 (control) | Not added | — | 0.09 | 100 | 0.19 | 152 |
| 11 (the invention) | Compound 1 | $0.9 \times 10^{-4}$ | 0.07 | 85 | 0.12 | 129 |
| 12 (the invention) | Compound 1 | $2.2 \times 10^{-4}$ | 0.05 | 80 | 0.09 | 120 |
| 13 (comparison) | Comparative Compound (a) | $1.4 \times 10^{-4}$ | 0.05 | 72 | 0.08 | 96 |

It can be seen from Table 3 that the compound of the invention gives improved results over Comparative Compound (a) with respect to sensitivity while preventing the formation of color development fog. Furthermore, a large increasing of sensitivity is obtained when the forced development is performed.

EXAMPLE 4

On a triacetate film base there was coated a first layer to a twelfth layer in the order described hereinafter to prepare a color reversal photographic light-sensitive material.

First Layer: Antihalation Layer

Gelatin layer containing black colloidal silver

Second Layer: Gelatin Intermediate Layer

Third Layer: Low-Sensitivity Red-Sensitive Emulsion Layer

This was prepared by adding the sensitizing dyes and cyan coupler emulsion as defined hereinafter to a low-sensitive silver iodobromide emulsion (silver iodide: 6.0 mol%, mean grain size: about 0.5 micron) which had been subjected to gold-sulfur sensitization.

Sensitizing Dyes: Anhydro-3,3'-di(γ-sulfopropyl)-5,5'-dichloro-9-ethylthiacarbocyanine sodium salt and anhydro-9-ethyl-3,3'-di(γ-sulfopropyl)-4,5,4',5'-dibenzothiacarbocyanine sodium salt Cyan Coupler Emulsion:

Coupler: 2-(Heptafluorobutyramido)-5-[2'-(2'',4''-di-tert-aminophenoxy)butyramido]phenol Coupler Solvent: Tricresyl phosphate The molar ratio of silver to coupler was 10.0/1 and the amount of silver coated was 0.7 g/m².

Fourth Layer: High-Sensitivity Red-Sensitive Emulsion Layer

This layer was prepared by adding the same sensitizing dyes and cyan coupler emulsion as used in the preparation of third layer to a high sensitive silver iodobromide emulsion (silver iodide: 6.0 mol%; mean grain size: about 0.7 micron) which had been subjected to gold-sulfur sensitization. The molar ratio of silver to coupler was 10.0/1, and the amount of silver coated was 0.9 g/m².

Fifth Layer: Gelatin Intermediate Layer

Sixth Layer: Low-Sensitivity Green-Sensitive Emulsion Layer

This was prepared by adding the sensitizing dyes and magenta coupler emulsion as defined hereinafter to a low sensitive silver iodobromide emulsion (silver iodide: 4 mol%; mean grain size: about 0.5 micron) which had been subjected to gold-sulfur sensitization.

Sensitizing Dyes: Anhydro-5,5',6,6'-tetrachloro-1,1'-diethyl-3,3'-di-γ-sulfopropylbenzimidazolocarbocyanine sodium salt and anhydro-3,3'-di(γ-sulfopropyl)-5,5'-diphenyl-9-ethyloxycarbocyanine sodium salt Magenta Coupler Emulsion:
  Coupler: 1-(2,4,6-Trichlorophenyl)-3-[3-(2,4-di-tert-amylphenoxyacetamido)benzamido]-5-pyrazolone
  Coupler Solvent: Tricresyl phosphate Seventh Layer: High-Sensitivity Green-Sensitive Emulsion Layer This layer was prepared by adding the same sensitizing dyes and magenta coupler emulsion as used in the preparation of sixth layer to a high sensitive silver iodobromide emulsion (silver iodide: 4 mol%; mean grain size: about 0.9 micron) which had been subjected to gold-sulfur sensitization. The molar ratio of silver to coupler was 10.0/1, and the amount of silver coated was 0.9 g/m².

Eighth Layer: Gelatin Intermediate Layer

Ninth Layer: Yellow Filter Layer
  Gelatin layer containing yellow colloidal silver Tenth Layer: Low-Sensitivity Blue-Sensitive Emulsion Layer This layer was prepared by adding the yellow coupler emulsion as defined hereinafter to a low sensitive silver iodobromide emulsion (silver iodide: 4 mol%; mean grain size: about 0.7 micron) which had been subjected to gold-sulfur sensitization.

Yellow Coupler Emulsion:
  Coupler: α-Pivaloyl-α-(1-benzyl-5-ethoxy-3-hydantoinyl)-2-chloro-5-hexadecylsulfonylaminoacetanilide
  Coupler Solvent: Triisononyl phosphate The molar ratio of silver to coupler was 7.0/1, and the amount of silver coated was 0.6 g/m².

Eleventh Layer: High-Sensitivity Blue-Sensitive Emulsion Layer

This layer was prepared by adding the same yellow coupler emulsion as used in the preparation of tenth layer to a high sensitive silver iodobromide emulsion (silver iodide: 4 mol%; mean grain size: about 1.0 micron) which had been subjected to gold-sulfur sensitization. The molar ratio of silver to coupler was 7.0/1, and the amount of silver coated was 1.2 g/m².

Twelfth Layer: Gelatin Protective Layer

To each emulsion layer was added a compound of the invention or Comparative Compound (a) as indicated in Table 4, and the additives as described below:

Stabilizer: 4-Hydroxy-6-methyl-1,3,3a,7-tetraazaindene

Hardener: 1,3-Bis-vinylsulfonylhydroxypropane

Coating Aids: Sodium p-dodecylbenzenesulfonate and sodium p-nonylphenoxypoly(ethyleneoxy)propanesulfonate In this way, Samples 21 to 25 were prepared.

TABLE 4

| Sample | Compound | Amount (mol/mol AgX) |
| --- | --- | --- |
| 21 (control) | Not added | — |
| 22 (the invention) | Compound 1 | $3.0 \times 10^{-4}$ |
| 23 (the invention) | Compound 1 | $5.0 \times 10^{-4}$ |
| 24 (comparison) | Comparative Compound (a) | $1.8 \times 10^{-4}$ |
| 25 (comparison) | Comparative Compound (a) | $2.8 \times 10^{-4}$ |

Just after coating, the material was stored at a temperature of 45° C. and a relative humidity of 80% for 3 days. After being stored at a temperature of 50° C. and a relative humidity of 20% for 3 days, each sample was exposed to light to an optical wedge and separation filters (Wratten 47B Filter produced by Kodak Limited, BPB-53 Filter produced by Fuji Photo Film Co., Ltd., and SS-60 Filter by Fuji Photo Film Co., Ltd.; the spectral transmittance of each filter is shown in the Figure). The material was subjected to the reversal color developing processing as described hereinafter. Thereafter, the photographic properties of the magenta color-forming layer were measured with the results shown in Table 5.

Developing Processing

| Steps | Temperature (°C.) | Time (min) |
| --- | --- | --- |
| 1. First Development | 38 | 6 |
| 2. Water-Washing | " | 2 |
| 3. Reversion | " | 2 |
| 4. Color Development | " | 6 |
| 5. Stopping | " | 2 |
| 6. Bleaching | " | 6 |
| 7. Fixing | " | 4 |
| 8. Water-Washing | " | 4 |
| 9. Stabilization | Ordinary temperature | 1 |
| 10. Drying | | |

The composition of the processing solution used at each step is as follows:

First Development

| | |
| --- | --- |
| Water | 700 ml |
| Sodium tetrapolyphosphate | 2 g |
| Sodium sulfite | 20 g |
| Hydroquinone monosulfonate | 30 g |
| Sodium carbonate (monohydrate) | 30 g |
| 1-Phenyl-4-methyl-4-methoxy-3-pyrazolidone | 2 g |
| Potassium bromide | 2.5 g |
| Potassium thiocyanate | 1.2 g |
| Potassium iodide (0.1% solution) | 2 ml |
| Water to make (pH = 10.1) | 1 liter |

Reversion

| | |
|---|---|
| Water | 700 ml |
| Nitrilo-N,N,N—trimethylenephosphonic acid 6 sodium salt | 3 g |
| Stannous chloride (dihydrate) | 1 g |
| Sodium hydroxide | 8 g |
| Glacial acetic acid | 15 ml |
| Water to make | 1 liter |

Color Development

| | |
|---|---|
| Water | 700 ml |
| Sodium tetrapolyphosphate | 2 g |
| Sodium sulfite | 7 g |
| Sodium tertiary phosphate (12 hydrate) | 36 g |
| Potassium bromide | 1 g |
| Potassium iodide (0.1% solution) | 90 ml |
| Sodium hydroxide | 3 g |
| Citrazinic acid | 1.5 g |
| 4-Amino-3-methyl-N—ethyl-β-hydroxyethylaniline sesquisulfate monohydrate | 11 g |
| Ethylenediamine | 3 g |
| Water to make | 1 liter |

Stopping

| | |
|---|---|
| Water | 700 ml |
| Sodium sulfite | 12 g |
| Sodium ethylenediaminetetraacetate (dihydrate) | 8 g |
| Thioglycerine | 0.4 ml |
| Glacial acetic acid | 3 ml |
| Water to make | 1 liter |

Bleaching

| | |
|---|---|
| Water | 800 ml |
| Sodium ethylenediaminetetraacetate (dihydrate) | 2 g |
| Iron (III) ammonium ethylenediaminetetraacetate (dihydrate) | 120 g |
| Potassium bromide | 100 g |
| Water to make | 1 liter |

Fixing

| | |
|---|---|
| Water | 800 ml |
| Sodium thiosulfate | 80 g |
| Sodium sulfite | 5 g |
| Sodium hydrogensulfite | 5 g |
| Water to make | 1 liter |

Stabilization

| | |
|---|---|
| Water | 800 ml |
| Formalin (30% by weight solution) | 5 g |
| Fuji Driwel (produced by Fuji Photo Film Co., Ltd.) | 5 ml |
| Water to make | 1 liter |

TABLE 5

| | Photographic Properties of the Magenta Color-Forming Layers | | | | | |
|---|---|---|---|---|---|---|
| | Just after Coating | | After 3 Days at 45° C. 80% RH | | After 3 Days at 50° C. 20% RH | |
| Sample | $D_{max}$ | Relative Sensitivity | $D_{max}$ | Relative Sensitivity | $D_{max}$ | Relative Sensitivity |
| 21 (control) | 3.2 | 100 | 3.1 | 89 | 2.8 | 124 |
| 22 (the invention) | 3.3 | 93 | 3.3 | 93 | 3.2 | 95 |
| 23 (the invention) | 3.4 | 90 | 3.4 | 90 | 3.3 | 92 |
| 24 (comparison) | 3.3 | 83 | 3.3 | 83 | 3.2 | 86 |
| 25 (comparison) | 3.4 | 79 | 3.4 | 79 | 3.3 | 82 |

In Table 5, $D_{max}$ represents the maximum density after the reversal processing. This corresponds to the color development fog at the usual negative development; i.e., as the $D_{max}$ is higher, less fog is formed by the negative development.

The relative sensitivity is a reciprocal number of the exposure amount providing a density which is one-half of the total of $D_{max}$ and $D_{min}$ of the reversal image, and is indicated as a relative value with that of Sample 21 just after coating as 100.

It can be seen from Table 5 that the compound of the invention is advantageous over Comparative Compound (a). There is a small reduction in sensitivity when the $D_{max}$ (corresponding to the color development fog at the negative development) of the reversal image is improved to the same level. Furthermore, it can be seen that even after storage of a color reversal film containing a vinyl sulfone-based hardening agent under high temperature and high humidity conditions or high temperature and low humidity conditions, the reduction in $D_{max}$ and sensitivity is very inhibited.

The same effect as above was obtained for the yellow color-forming layer and cyan color-forming layer.

While the invention has been described in detail and with reference to specific embodiments thereof, it will be apparent to one skilled in the art that various changes and modifications can be made therein without departing from the spirit and scope thereof.

What is claimed is:

1. A process for developing a color photographic light-sensitive material which comprises exposing a color photographic light-sensitive material and, thereafter, color developing the exposed light-sensitive material in the presence of a compound represented by the general formula (I):

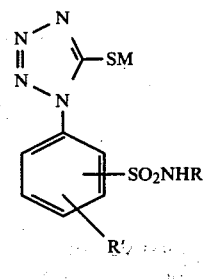

wherein M is a hydrogen atom, an alkali metal atom, NH$_4$ or a protective group for the mercapto group which undergoes cleavage by the action of an alkali; R is a hydrogen atom or an alkyl group containing 1 to 3 carbon atoms; and R' is a hydrogen atom or an alkyl group containing 1 to 3 carbon atoms in an amount effective to prevent the formation of development fog while minimizing the inhibition of color development and reduction of sensitivity.

2. A process for developing a color photographic light-sensitive material as claimed in claim 1, wherein R is hydrogen.

3. A process as claimed in claim 1, wherein the compound of general formula (I) is contained within the light-sensitive material in an amount of $10^{-7}$ to $10^{-2}$ mol/Ag mol.

4. A process for developing a color photographic light-sensitive material as claimed in claim 3, wherein the compound of general formula (I) is contained in the light-sensitive material in an amount of $10^{-6}$ to $10^{-2}$ mol/Ag mol.

5. A process for developing a color photographic light-sensitive material as claimed in claim 1, wherein the compound of general formula (I) is contained in the color developer in an amount of $10^{-6}$ to $10^{-1}$ mol/l.

6. A process for developing a color photographic light-sensitive material as claimed in claim 5, wherein the compound of general formula (I) is contained in the color developer in an amount of from $10^{-5}$ to $3 \times 10^{-2}$ mol/l.

7. A process for developing a color photographic light-sensitive material as claimed in claim 1, wherein said process is carried out at a temperature of from 18° C. to 50° C.

8. A process for developing a color photographic light-sensitive material as claimed in claim 7, wherein said process is carried out over a period of 10 seconds to 12 minutes.

9. A process according to claim 1, wherein the color photographic light-sensitive material contains a vinyl sulfone-based compound as a hardener.

10. A process according to claim 1, wherein a time for the color developing is lengthened than a normal developing time.

11. A process according to claim 1 wherein R is a hydrogen atom.

* * * * *